United States Patent
Hussey

(10) Patent No.: US 7,181,779 B2
(45) Date of Patent: Feb. 27, 2007

(54) SPORT GOGGLE WITH SIDE VENT FOR IMPROVED VENTILATION

(75) Inventor: Patrick P. Hussey, Carlsbad, CA (US)

(73) Assignee: K-2 Corporation, Seattle, WA (US)

( * ) Notice: Subject to any disclaimer, the term of this patent is extended or adjusted under 35 U.S.C. 154(b) by 81 days.

(21) Appl. No.: 10/763,361

(22) Filed: Jan. 23, 2004

(65) Prior Publication Data

US 2005/0160521 A1  Jul. 28, 2005

(51) Int. Cl.
*A61F 9/02* (2006.01)

(52) U.S. Cl. .................. 2/436; 2/437; 2/452; 2/426; 2/431

(58) Field of Classification Search .............. 2/436, 2/437, 452, 426, 431, 432, 438, 439, 440, 2/441, 447, 428

See application file for complete search history.

(56) References Cited

U.S. PATENT DOCUMENTS

| | | | |
|---|---|---|---|
| 2,399,991 A * | 5/1946 | Desimone et al. ......... 2/437 |
| 2,409,286 A | 10/1946 | Joyce | |
| 2,877,463 A * | 3/1959 | Watkins ................. 2/437 |
| 3,141,172 A | 7/1964 | Hirschmann | |
| 3,418,658 A | 12/1968 | Danico | |
| 3,517,393 A | 6/1970 | Beauchef | |
| 4,141,085 A | 2/1979 | Adams, Sr. | |
| 4,172,455 A | 10/1979 | Beaussant | |
| 4,290,673 A | 9/1981 | Yamamoto | |
| 4,435,852 A | 3/1984 | Nesler | |
| 4,649,577 A | 3/1987 | Wiedner | |
| 4,653,124 A | 3/1987 | McNeal et al. | |
| 4,670,914 A | 6/1987 | Harris | |
| 4,704,746 A | 11/1987 | Nava | |
| 4,877,320 A | 10/1989 | Holden | |
| 4,977,627 A | 12/1990 | Metcalfe et al. | |
| 5,363,512 A | 11/1994 | Grabos, Jr. et al. | |
| 5,452,480 A | 9/1995 | Ryden | |
| 5,519,896 A | 5/1996 | Ford | |
| 5,542,130 A | 8/1996 | Grabos, Jr. et al. | |
| 5,610,668 A | 3/1997 | Mage | |
| 5,652,965 A | 8/1997 | Crooks | |
| 5,657,106 A | 8/1997 | Herald, Jr. et al. | |
| 5,771,499 A | 6/1998 | Monaco et al. | |
| 5,966,746 A | 10/1999 | Reedy et al. | |
| 6,009,564 A | 1/2000 | Tackles et al. | |
| 6,038,707 A | 3/2000 | Ryden et al. | |
| 6,076,196 A * | 6/2000 | Masumoto ............... 2/436 |
| 6,119,276 A | 9/2000 | Newcomb et al. | |
| 6,138,285 A | 10/2000 | Robrahn et al. | |
| 6,425,143 B1 | 7/2002 | Benedict et al. | |
| 6,513,171 B1 | 2/2003 | Soper | |
| 6,550,914 B1 | 4/2003 | Kopfer | |
| 6,637,038 B1 | 10/2003 | Hussey | |

* cited by examiner

FOREIGN PATENT DOCUMENTS

DE  3503393 A1  8/1986

*Primary Examiner*—Katherine Moran
*Assistant Examiner*—Richale L. Haney
(74) *Attorney, Agent, or Firm*—Christensen O'Connor Johnson Kindness PLLC

(57) ABSTRACT

An improved sport goggle for skiing, motorcycling, paintball, racing, and other sports featuring clip-mounted side apertures communicating with the eye cavity of the goggle through adjacent venting apertures. Venting of the eye cavity of the sport goggle is aided by forming of the clip shape to create low pressure zones adjacent to the side venting apertures. The clips are rotationally attached to the goggle to provide an adjustable mount for the strap around heads or helmets while still forming the negative air pressure zone in all rotated positions. The clips may also be provided in a kit of differently dimensioned clips to adjust the negative air pressure venting characteristics of the clips and goggle to the intended sport or task.

9 Claims, 2 Drawing Sheets

SPORT GOGGLE WITH SIDE VENT FOR IMPROVED VENTILATION

BACKGROUND OF THE INVENTION

1. Field of the Invention

The present invention relates to an improved goggle for sports and other activities where eye protection and improved vision are desirable. More particularly it relates to a goggle which incorporates a system of high and low pressure areas external to the goggle to increase ventilation of the enclosed eye cavity to prevent fogging of the goggle lens. The disclosed device additionally features increased ventilation from side vents which communicate through a clip also used for strap attachment. This clip is rotationally engaged with the body of the goggle and allows for attachment of the head strap to the goggle on one side of the clip with the opposite side rotationally engaged to the body of the goggle. This rotational attachment may be by hinge, flexible flap in an extension, or other means of attachment to allow for the rear end of the clip to rotate away from the goggle body.

An aperture formed in the clip between the strap and body engagement creates the negative pressure adjacent to the side aperture of the goggle body. Further, engaging the clip to the goggle in a hinged or rotational attachment allows for rotation of the clip and aperture toward and away from the goggle. This provides for increased air flow over the aerodynamic surface of the leading edge of the clip and provides increased negative air pressure external to a side vent in the body when the goggle is being worn with or without a helmet. This rotational or hinged engagement is especially important when goggles are used in combination with protective helmets for skiing, motorcycling, auto racing, and other endeavors which require both eye protection and cranial protection.

Further, if the clip is removably attachable to the goggle body, it allows for a kit of such clips to be provided to users of the goggle. Such a kit can include clips with leading edges having shapes to maximize air speed over the trailing aperture in the clip for the sport or task at hand. Additionally, the kit of different shaped and dimensioned clips can include clips with differently sized apertures to thereby optimize the air drawn through the aperture in the clip from the adjacent side venting aperture communicating with the eye cavity. This would provide the user with the ability to change not only the shape of the clip to maximize air flow for the task at hand, but to also change the size of the clip aperture for the task. Skiers can thus adjust for optimum air speed of the airflow over the aperture and venting size of the aperture as can motorcyclists, parachutists, any users for an infinite number of sports and tasks that require wearing goggles but need to customize airflow for the task.

Using the variable shape of the clip and the variable aspects of the aperture in the clip, it is also anticipated that a non hinged engagement to the goggle body might be used since not every user would require such a function. Consequently in another preferred embodiment of the device, the clip would removably attach to the body using a means of attachment which secures it to the body to hold the strap, but does not necessarily rotate toward and away from the body itself. The user can then simply change the clip shape and/or aperture dimensions for optimum results for their intended task. Such an embodiment could also have the pair of clips attached to the head band with the user having a kit of assembled head bands with clips thereon adapted for attachment to the goggle body with each such assembled clip and headband having different clip apertures and/or exterior surface dimensions to maximize airflow over the clip aperture during the intended use.

2. Prior Art

Skiing, motorcycling, paintballing, field hockey, lacrosse, auto racing, and other sports which incorporate goggles for eye protection have become an ever more popular recreational pastime in the United States and throughout the world. It has also become fashionable for safety reasons for participants in such hazardous sports to wear both eye protection as well as head protection. Goggles are also especially a virtual requirement for the military in areas with blowing sand or during parachute jumps and similar operations and when employed, are generally used in combination with a protective helmet.

Since goggles are generally worn over the eyes of a user, it is most important that the eyesight of the user not be impaired by the goggles being worn and if possible, be improved by the goggles covering the eyes. In cold climates and in freezing venues such as ski slopes and high altitudes an inherent problem encountering goggle wearing individuals is that of fogging of the goggle lens.

Fogging is generally caused by the temperature differential created in the enclosed area formed behind the goggle lens and in front of the face of the wearer and the air exterior to the goggle. The face of the user radiates heat and tends to heat the air inside the goggle cavity behind the lens much like the windshield of a car tends to fog when the air inside the car is warmer than the air outside the car, thus causing fog or condensation on the window. Consequently, venting of the air inside the goggle cavity behind the lens is essential to help overcome and prevent fogging of the lens that would inhibit the view of the wearer. Various patents have attempted to overcome the inherent tendency of goggles to fog in a cold environment.

U.S. Pat. No. 6,009,564, (Tackles) teaches a vented goggle; however, Tackles requires a plurality of tunnels or slots be formed in the mask portion of the goggle which are easily plugged by snow and especially ice if the skier falls or by dirt in a blowing sand environment. Tackles also lacks a low pressure system to pull air from the face cavity.

U.S. Pat. No. 5,652,965 (Crooks) teaches a non-fogging goggle, but Crooks also uses an elongated slot formed in the mask portion below the lens that is easily clogged and also lacks negative pressure venting.

U.S. Pat. No. 5,542,130 (Grabos) discloses goggle with a ventilation adjustment assembly having a plurality of apertures in the lens with a shutter to close them to adjust the flow of air. Grabos lacks a focused air flow on the apertures and any negative pressure to pull air from the cavity it creates.

U.S. Pat. No. 4,670,914 (Harris) teaches venting of a goggle like device. However, Harris lacks any positive pressure or negative pressure to aid in the flow.

U.S. Pat. No. 4,290,673 (Yamamoto) discloses ski goggles which have a heating means to heat the space between two lenses but lacks any pressurized low pressure evacuation of air from the internal cavity.

As such, there is a pressing need for a non-fogging goggle that will work in cold, dusty, and other harsh environments. Such a goggle should have air venting that is aided by exhaust vents having negative pressure which evacuate the goggle cavity behind the lens. Additionally such a goggle could increase air pressure entering the cavity yielding an increase in pressure differential with the exhaust cavity increasing air flow. Such a device would be further enhanced by the provision of filters to absorb moisture, prevent back flow of particulate into the goggle cavity, or regulate the amount of air moving through the device and allow for adjustment thereof. Finally such a device should provide for an angle adjustable engagement of the strap to the goggle for use with a helmet, or large and small head sizes, while concurrently providing an aerodynamic surface to increase airspeed to thereby increase negative pressure adjacent to the exhaust apertures.

SUMMARY OF THE INVENTION

Applicant's device is an improved goggle for use in skiing, snowboarding, motorcycling, motocross, paintball, military operations, and other sports and endeavors where the use of non-fogging goggles is favored or required. The device features one or a plurality of intake apertures on one or a combination of the goggle lens and body, which communicate with the eye chamber formed between the lens and the face of the wearer inside the goggle when mounted to a face. These intake apertures communicating air to the eye cavity are best positioned in a plurality of points on the front face of the goggle when worn by the user. In any case, at least one aperture communicates through the lens, or the body of the goggle which holds the lens, and receives air from the frontal area of the goggle in the as-worn position on the face of the user. A lower intake aperture underneath the lip traversing over the user's nose may also be provided to communicate air pressurized from the air hitting the wearer's face and forced into the lower intake aperture by the protruding body of the goggle.

A plurality of different air intake apertures, best positioned in both sides of the goggle, would thus communicate exterior air into the eye chamber. At least one, and preferably a plurality of side exhaust apertures would be positioned on the side of the goggle body to vent air to the atmosphere from the eye chamber. In the currently disclosed device, this venting from the eye cavity from the side apertures is aided by a leading edge of the two sides of the goggle body being curved much like an airplane wing and creates lift and a resulting low pressure area immediately adjacent to the side venting apertures adjacent to clip apertures communicating through the clip, to draw air out through these side venting apertures.

The provision of this unique apertured clip, also provides for an increase in airflow over the clip aperture through the provision of an aerodynamic front portion of the clip which increases air speed over a trailing aperture in the clip thereby creating increased negative air pressure adjacent to the clip aperture communicating through the clip. The clip aperture is positioned in the clip to communicate with, or be positioned immediately adjacent to, the side exhaust apertures in the body of the goggle, with the clip attached to the goggle, to draw air through the side apertures and through the clip apertures.

An optional insertable moisture trap, or dust filter, filled with appropriate absorbent material is dimensioned for cooperative engagement into one or both of the side venting apertures and the clip aperture, to aid in the adsorption of moisture from the eye chamber, and/or to prevent back flow through the side exhaust aperture or the clip aperture of dust, debris, or moisture into the eye cavity.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention.

It is an object of this invention to provide a goggle with one or a plurality of intentionally directed air flows into front facing intake one or more apertures to help pressurize the air flowing into the eye chamber of the goggle.

Another objective of this invention is to provide such an improved goggle which uses shaped side and top edges adjacent to the lens to create low pressure zones adjacent to top and especially side vent apertures to draw air from the eye chamber.

An additional objective of this invention is to provide optionally insertable filter cartridges containing moisture and/or particulate absorbent material to prevent communication of moisture and particulate to the eye cavity.

A still further object of this invention is the provision of air directional components that are not easily clogged by snow, ice, dirt, or paintballs, and which can be easily cleaned.

These together with other objects of the invention, along with the various features of novelty, which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred and alternate embodiments of the invention. There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

BRIEF DESCRIPTION OF DRAWING FIGURES

DETAILED DESCRIPTION OF PREFERRED EMBODIMENTS OF THE DISCLOSED DEVICE

Figure 1:
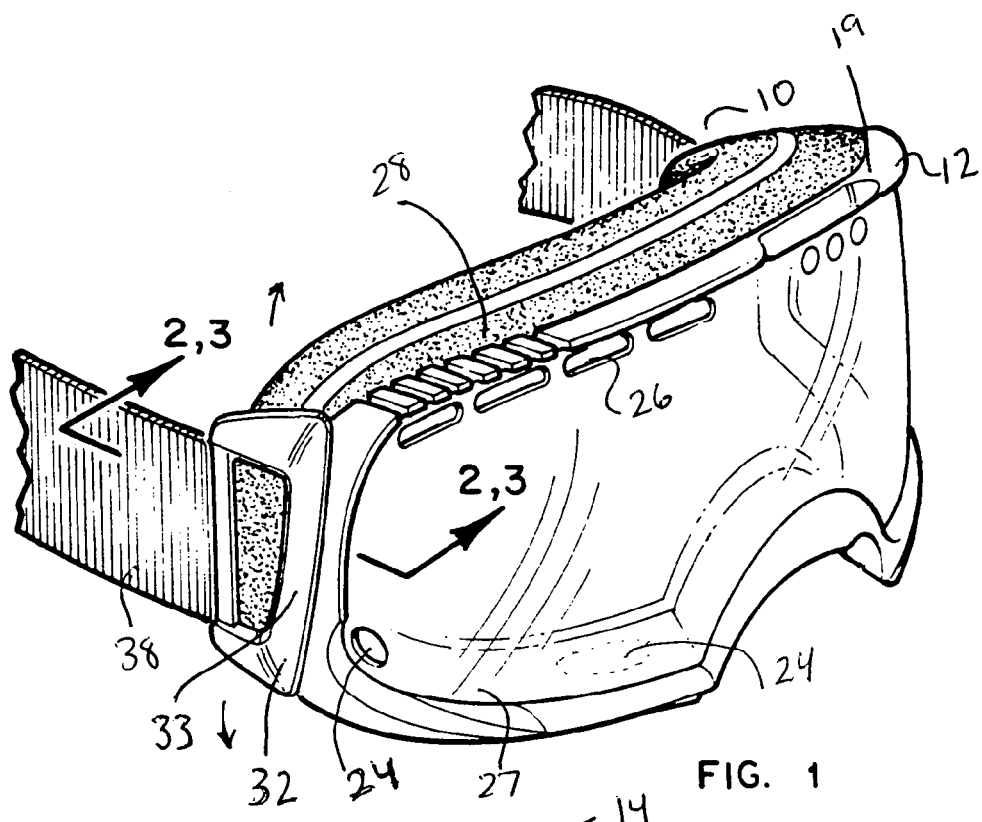
FIG. 1 is a perspective view of the disclosed device depicting the goggle body having clips engaged on two sidewalls of the body at the leading edge of the clip and with the head strap at the trailing end of the clip.

Referring now to the drawings FIG. 1–4 wherein similar parts of the invention are identified by like reference numerals, the figures disclose the improved sport goggle 10 featuring improved air extraction using directed aerodynamic airflow. The goggle body 12 is shaped to conform to a human face on the inside surface 14 which is conventionally covered in foam or similar soft material. The goggle lens 16 is operatively mounted in the body 12 and conventionally is best curved around the face of the user to provide side viewing. In use as worn on a user, an eye cavity 18 is formed and best defined by the area between the user's face, the inside surface 20 of lens 16, the top wall 19, the sidewalls 21, and the bottom wall or ledge 27.

The lens 16 in the current best mode of the device 10 would be a unitary lens featuring two lenses separated by an insulating space 29 to help therebetween to reduce fogging, although the disclosed air evacuation system herein will also enhance the anti fogging characteristics of a single lens goggle and use with any single or multiple lens goggle is anticipated.

One or a plurality of intake apertures facing toward the front of the goggle 12 when worn on the user's face are provided for the ingress of air from the exterior to the eye cavity 18. Such intake apertures may be situated in one, a plurality, or all of, lower intake apertures 24 below the ledge 27, body intake apertures 25 formed in the body 12, and upper intake apertures 26 formed in the lens 16 or the top wall 19. The design and ornamental aspects of the individual goggle will generally dictate which individual or combination of intake apertures are provided. However, at least one intake aperture must be provided to communicate exterior air into the eye cavity 18.

Venting of the eye cavity 18 is provided by the side venting apertures 30 communicating through the sidewalls 21 on either side of the lens 16. As shown in FIG. 1 the goggle body 12, adjacent to the side venting apertures 30 has clips 32 engaged on the two sidewalls 21. This engagement in the rotating or translating clip 32 in the first preferred embodiment of the device 10 features a rotational or hinged engagement of the clip 32 to the sidewall 21 the leading edge of the clip 32. The strap 38 or other elastic means of pulling the goggle snugly against the user's face, is attached to the clip 32 the trailing edge of the clip 32 with the clip aperture 34 communicating through the clip 30 between the leading edge and trailing edge.

Figure 2:
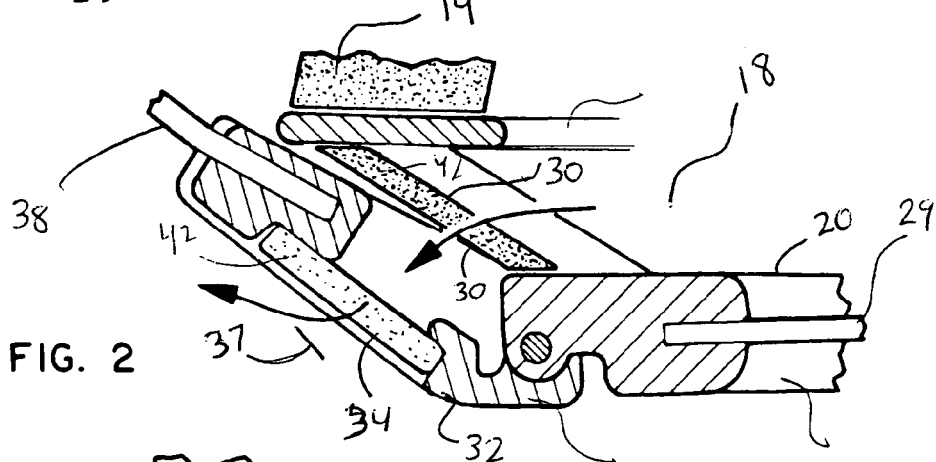
FIG. 2 is a cut away view of through line 2 of FIG. 1 showing the rotating clip in its closest position to the sidewall of the goggle body and the resulting air flow through the exit aperture in the sidewall communicated through the clip aperture in the clip.
Figure 3:
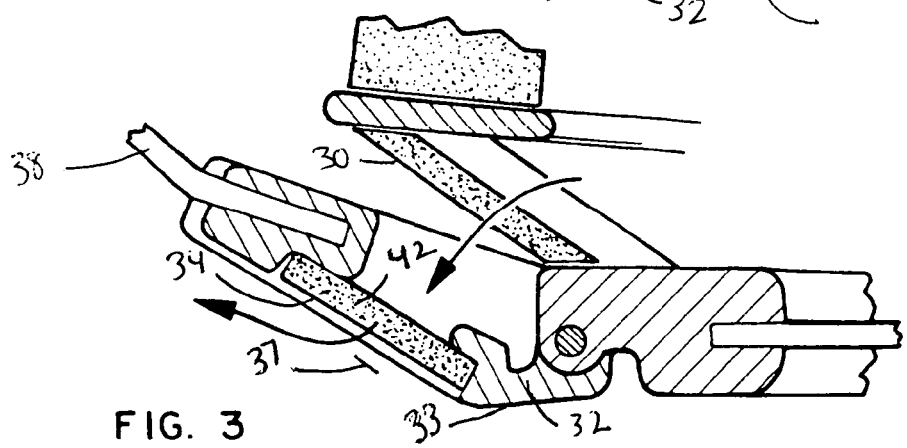
FIG. 3 is a top view of line 3 of FIG. 1 showing the clip translated away from the sidewall of the goggle body and the resulting air flow through the exit aperture in the sidewall communicated through the clip aperture in the clip.
Figure 4:
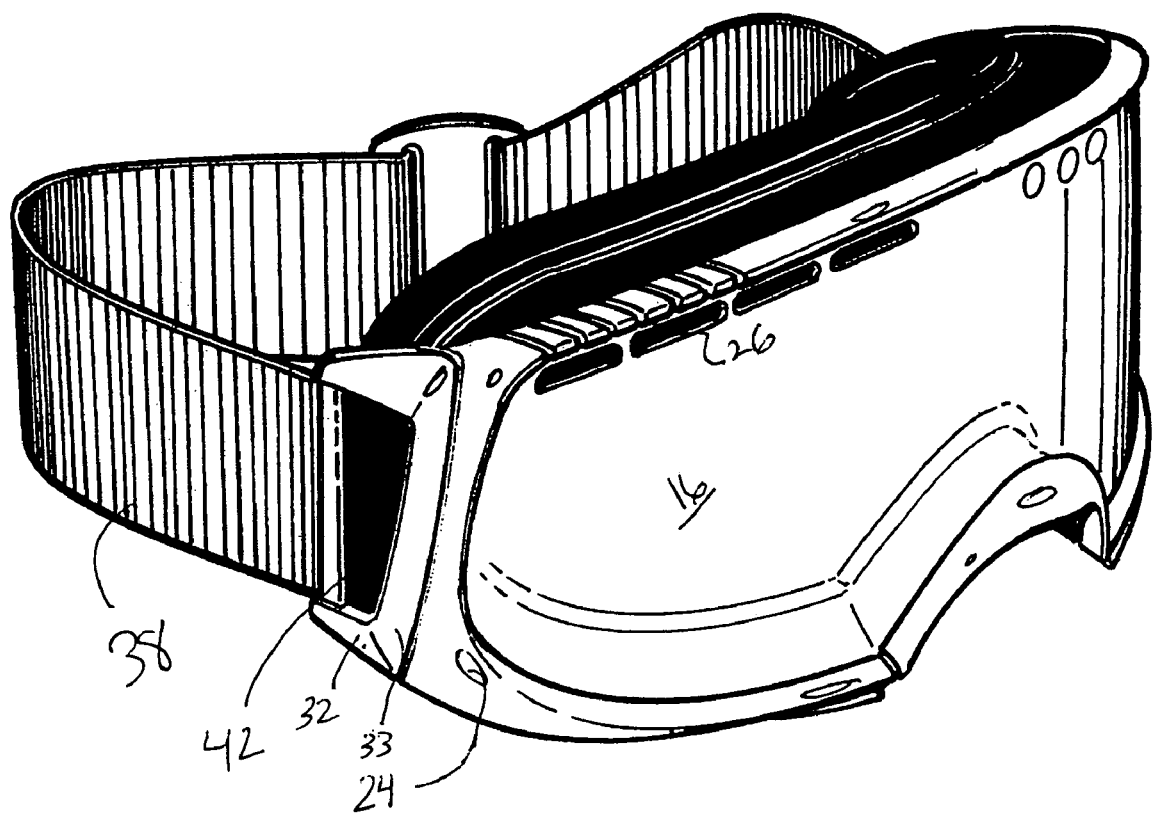
FIG. 4 depicts another preferred embodiment of the device wherein the clip is fixedly attached, or formed integrally to the sidewall and dimensioned forward of the aperture to proved an aerodynamic approach in front of the clip aperture to increase airflow thereover.

The clip 32 being rotationally affixed to the sidewall 21 at its leading edge will translate toward and away from the sidewall 21 between an infinite number of positions between a retracted position and an extended position. In the retracted position as best shown in FIG. 2, the clip 30 in its closest position adjacent to the sidewall 21 of the goggle body 12. This position would be achieved on a user with a small head who is not wearing a helmet. When in the retracted position, the inside surface of the clip 32 would be contacting the surface of the sidewall 21 and the resulting air flow through the side venting aperture 30 in the sidewall communicates immediately through the clip aperture 34 in the clip 32.

In users with a large head, or when the user is wearing a helmet or hat with the strap 38 circumventing the exterior of the headgear, the clip 32 will rotate on its engagement with the sidewall 21 at its leading edge and translate away from the sidewall 21 of the goggle body 12 with the resulting air flow through the side venting aperture 30 still being communicated through the clip aperture 34 with the additional path through a small gap 40 formed between the translated clip 32 and the sidewall 21.

In use, for skiing, snowboarding, motorcycling, motocross, paintball, military operations, and other sports and endeavors where non-fogging goggles are best employed, exterior air is communicated to the eye cavity 18 through the aforementioned combination of one or a plurality of intake apertures individually or combined. Forward movement by the user wearing the goggle increases air pressure into the intake apertures aiding in moving pressurized air into the eye cavity 18 through the intake apertures.

The side venting apertures 30 are thus provided to vent air from the eye cavity 18 to the exterior atmosphere. As noted above, this venting from the eye cavity 18 from the side apertures is greatly enhanced by the clip aperture 34 and clip aerodynamic exterior dimensions. An aerodynamic shape or curve of the clip 32 at the leading edge 33, immediately in front of the clip aperture 34, acts to increase airspeed over the clip aperture 34 in the direction of the trailing edge of the clip 32 much like the curved front edge of a wing on an airplane increases the airspeed over the top of the wing. The increased air speed over the clip aperture 34 thereby creates a negative air pressure zone immediately adjacent to the clip aperture 34 communicating through the clip 32. The clip aperture 34 is positioned in the clip 32, to communicate immediately adjacent to the side venting aperture 30 which communicates with the eye cavity 18. The negative air pressure zone formed adjacent to the clip aperture 34 thereby acts to actively draw air through the side venting apertures 30 from the eye cavity 18 when the user is moving and forcing air over the leading edge of the clip 32. The clip 32, whether in the retracted position, or in the extended position with a helmet on the user benefits from the leading edge of the clip 32 being aerodynamic in shape, and its continual close proximity to the sidewall 21 at the leading edge which is enabled by the hinged or other rotational engagement at the leading edge. This provides benefits from the increased air speed over the leading edge at all times resulting in the negative pressure zone adjacent to the clip aperture 34 no matter its position. As shown, a mount of the clip 32 to the sidewall 21 at the leading edge 33 is best done in a fashion that creates little or no gap between the clip 32 and the sidewall 21 when in the retracted position. The end result is enhanced airflow provided by the clip aperture 34 and the negative air pressure zone 37 adjacent thereto through all positions of the clip 32 from the retracted position through the extended position and the resulting venting of the eye cavity 18 and elimination of fogging.

Also shown in FIG. 1–4 is the optional insertable moisture trap, or dust filter 42, of appropriate filter or absorbent material and dimensioned for cooperative engagement into one or both of the side venting apertures 30 and the clip aperture 34, to aid in the adsorption of moisture from the eye chamber, and/or to prevent back flow through the side venting aperture 30 or the clip aperture 34 of dust, debris, or moisture into the eye cavity 18. In the current preferred mode of the device 10, the dust filter 42 positioned in the clip aperture 34 provides an additional flat surface over which air may travel during acceleration.

As noted above, FIG. 4 depicts another preferred embodiment of the device wherein the clip 32 is fixedly attached to the sidewall 21 using a means of attachment such as a slidable engagement over a rail on the sidewall engaged with a slot on the clip 32 shown in FIG. 4. Or the aerodynamically shaped clip 32 might also be formed integral to the sidewall 21 and dimensioned at the leading edge 33 forward of the clip aperture 34 to provide the aerodynamic approach in front of the clip aperture 34 to increase airflow thereover. This embodiment would use material for the clip 32 or sidewall 21 or both when engaged, of sufficient flexibility to provide for some sideways movement to accommodate large heads or helmets, and still provide the aerodynamic increase in air speed in front of the clip aperture 34. If formed integral to the sidewall 21 or permanently mounted on the sidewall 21, it is important to provide a means for engagement of the strap 38 which is to the rear of the clip aperture 34 to avoid impeding the airflow through the clip aperture 34 to the negative air pressure zone 37.

Finally, as noted above, if the clip 32 is removably attachable to the goggle body 12, it allows for the provision to the user of a kit of such clips 32. Such a kit can include a plurality of different clips 32 with leading edges 33 having varying shapes to optimize air speed over the trailing clip aperture 34 in the clip for the sport or task at hand. Additionally, such a kit of differently dimensioned clips 32 can include clips 32 with varying sized clip apertures 34 to thereby optimize the air drawn through the clip aperture 34 from the side venting aperture 30 communicating with the eye cavity 18. Variable sized clip apertures 34 provide the user with the utility to change not only the shape of the clip to maximize air flow for the task at hand, but to vary the flow through characteristics through the side venting apertures 30 from the eye cavity 18. Skiers can thus adjust for optimum air speed of the airflow over the aperture and venting size of the aperture as can motorcyclists, parachutists, any users for an infinite number of sports and tasks that require wearing goggles but need to customize airflow for the task.

While all of the fundamental characteristics and features of the sport goggle with hinged side vent for the prevention of fogging have been described herein, with reference to particular embodiments thereof, a latitude of modification, various changes and substitutions are intended in the foregoing disclosure, and it will be apparent that in some instances, some features of the invention may be employed without a corresponding use of other features without departing from the scope of the invention as set forth. It should be understood that such substitutions, modifications, and variations may be made by those skilled in the art without departing from the spirit or scope of the invention. Consequently, all such modifications and variations are included within the scope of the invention as defined herein.

What is claimed is:

1. A sport goggle for wearing on the face of a user having an improved air venting system to enhance air flow through the goggle, comprising:
   a goggle body having an exterior surface and an interior surface and having a lens aperture surrounded by a top wall, a bottom wall, and two sidewalls;
   a lens mounted in said lens aperture;
   an eye cavity defined by the area between said interior surface, said lens, said top wall, said bottom wall, and said two sidewalls;
   at least one side venting aperture communicating through one of said sidewalls of said goggle body with said eye cavity;
   at least one clip, said clip having a leading edge and a trailing edge connected by a pair of side edges, an interior clip surface, and an exterior clip surface;
   a clip aperture communicating through said clip between said interior surface and said exterior surface;
   means of attachment of said clip to one of said two sidewalls;
   said exterior surface of said clip between said clip aperture and said leading edge dimensioned to create a low air pressure area immediately adjacent to said clip aperture when moving air travels over said leading edge, whereby air flow exhausting from said eye cavity through side venting aperture is enhanced by the force of said low pressure area acting to draw higher pressure air from said eye cavity through said side venting aperture; and
   wherein the means of attachment of said clip to said sidewall is a rotational engagement of said clip to said sidewall; and said rotational engagement engaging said clip to said sidewall at an attachment point wherein said trailing edge is translatable between a retracted position closest to said sidewall to an extended position, distanced from said sidewall, when said clip is rotated in said rotational engagement.

2. The sport goggle as defined in claim 1 wherein said attachment point is adjacent to said leading edge thereby maintaining said leading edge substantially adjacent to said sidewall when said trailing edge moves between said retracted position and said extended position.

3. The sport goggle as defined in claim 2 further comprising means for attachment of a strap to said trailing edge.

4. The sport goggle as defined in claim 2 wherein said rotational engagement of said clip to said sidewall comprises a hinged engagement of said clip to said sidewall.

5. The sport goggle as defined in claim 4 wherein said hinged engagement of said clip to said sidewall engages said interior surface of said clip to said sidewall thereby minimizing airflow interruption over said exterior surface of said clip.

6. The sport goggle as defined in claim 1 further comprising means for attachment of a strap to said trailing edge.

7. The sport goggle as defined in claim 1 wherein said rotational engagement of said clip to said sidewall comprises a hinged engagement of said clip to said sidewall.

8. The sport goggle as defined in claim 7 wherein said hinged engagement of said clip to said sidewall engages said interior surface of said clip to said sidewall thereby minimizing airflow interruption over said exterior surface of said clip.

9. A sport goggle for wearing on the face of a user having an improved air venting system to enhance air flow through the goggle, comprising:
   a goggle body having an exterior surface and an interior surface and having a lens aperture surrounded by a top wall, a bottom wall, and two sidewalls;
   a lens mounted in said lens aperture;
   an eye cavity defined by the area between said interior surface, said lens, said top wall, said bottom wall, and said two sidewalls;
   at least one intake aperture communicating through said lens or said goggle body with said eye cavity;
   at least one side venting aperture communicating through one of said sidewalls of said goggle body with said eye cavity;
   at least one clip, said clip having a leading edge and a trailing edge connected by a pair of side edges, an interior clip surface, and an exterior clip surface;
   a clip aperture communicating through said clip between said interior surface and said exterior surface;

means of attachment of said clip to one of said two sidewalls;

said exterior surface of said clip between said clip aperture and said leading edge dimensioned to create a low air pressure area immediately adjacent to said clip aperture when moving air travels over said leading edge, whereby air flow exhausting from said eye cavity through said venting aperture is enhanced by the force of said low pressure area acting to draw higher pressure air from said eye cavity through said venting aperture;

wherein the means of attachment of said clip to said sidewall renders said clip removably engageable to said sidewall; and means for attachment of a strap to said trailing edge.

* * * * *